(12) United States Patent
Gottlob

(10) Patent No.: US 11,568,972 B2
(45) Date of Patent: Jan. 31, 2023

(54) WORKFLOW PLATFORM TO INTEGRATE WITH AN ELECTRONIC HEALTH RECORD SYSTEM

(71) Applicant: COMMURE, INC., San Francisco, CA (US)

(72) Inventor: Falk Gottlob, San Rafael, CA (US)

(73) Assignee: COMMURE, INC., San Francisco, CA (US)

( * ) Notice: Subject to any disclaimer, the term of this patent is extended or adjusted under 35 U.S.C. 154(b) by 0 days.

(21) Appl. No.: 17/227,613

(22) Filed: Apr. 12, 2021

(65) Prior Publication Data

US 2022/0328145 A1    Oct. 13, 2022

(51) Int. Cl.
| | |
|---|---|
| G16H 10/60 | (2018.01) |
| G16H 80/00 | (2018.01) |
| G06F 16/955 | (2019.01) |
| G06F 21/31 | (2013.01) |

(52) U.S. Cl.
CPC ......... *G16H 10/60* (2018.01); *G06F 16/9558* (2019.01); *G06F 21/31* (2013.01); *G16H 80/00* (2018.01)

(58) Field of Classification Search
CPC .............................. G06F 16/9558; G06F 21/31
See application file for complete search history.

(56) References Cited

U.S. PATENT DOCUMENTS

| | | | | |
|---|---|---|---|---|
| 9,171,285 | B2 * | 10/2015 | Greene ................ | G06Q 10/087 |
| 2010/0131293 | A1 * | 5/2010 | Linthicum ............ | G16H 10/60 |
| | | | | 715/838 |
| 2010/0131482 | A1 * | 5/2010 | Linthicum ............ | G06F 19/00 |
| | | | | 707/706 |
| 2014/0278533 | A1 * | 9/2014 | D'Souza ............... | G16H 10/60 |
| | | | | 705/3 |
| 2016/0291847 | A1 * | 10/2016 | Lee ...................... | G06F 3/04847 |
| 2017/0068690 | A1 * | 3/2017 | Harlamert ........... | G06Q 30/0201 |
| 2017/0357759 | A1 * | 12/2017 | Stepaniuk ............ | G06Q 10/10 |
| 2018/0121612 | A1 * | 5/2018 | Connely, IV ........ | G16H 40/63 |
| 2020/0234444 | A1 * | 7/2020 | Budman ............... | G06T 7/12 |

FOREIGN PATENT DOCUMENTS

WO    WO-2015195315 A1 * 12/2015 ............. G10L 15/26

* cited by examiner

*Primary Examiner* — Jonathan Durant
*Assistant Examiner* — Anne-Marie K Alderson
(74) *Attorney, Agent, or Firm* — Sterne, Kessler, Goldstein & Fox P.L.L.C.

(57) ABSTRACT

A system and method for integrating a workflow platform with an electronic health record system (EHRS) is disclosed. The system and method includes at least: receiving from the EHRS, a context tag embedded in a screen of the EHRS that is currently being presented to a user, where the context tag includes: an authentication parameter identifying the user accessing the screen, and a context identification parameter identifying a context of the screen. Authentication is performed to authenticate the user based on the authentication parameter. Based on authenticating the user, launch of the workflow platform is initiated. The workflow platform is populated with data retrieved based on the context identification parameter such that which data is retrieved depends on the context identification parameter.

20 Claims, 5 Drawing Sheets

WORKFLOW PLATFORM TO INTEGRATE WITH AN ELECTRONIC HEALTH RECORD SYSTEM

TECHNICAL FIELD

Embodiments relate to systems that integrate with an electronic health record (EHR) system, specifically to a system to integrate a workflow platform with an EHR system.

BACKGROUND

An EHR system is an enterprise software application commonly used to allow healthcare providers, such as doctors, nurses, clinicians, hospitals, labs, and clinics, etc., to electronically access, store, and maintain patient health information in a digital format, and to share the patient health information across different healthcare settings. The patient health information can include a range of data, including patient demographics data, medical history, medication, allergies, immunization status, laboratory test results, radiology images, vital signs, personal statistics like age and weight, and billing information, as examples.

EHR systems are a drastic improvement over paper-based medical records. Paper-based medical records require a large amount of storage space. Paper records are often stored in different locations, and different medical professionals may each have different and incomplete records about the same patient. Obtaining paper records from multiple locations for review by a health care provider may be time consuming and complicated. In contrast, in EHR systems data is stored in digital format, and thus may be accessed from anywhere. EHR systems significantly simplify the reviewing process for health care providers. Because data in EHR systems is much more accessible, coordination of medical care is vastly improved.

EHR systems also decrease the risk of misreading errors by health care professionals. Poor legibility is often associated with handwritten, paper medical records, which can lead to medical errors. Data in EHR systems, on the other hand, is inherently legible given that it is typically stored in typeface. In addition, EHR systems enhance the standardization of forms, terminology and abbreviations, and data input, which help ensure reliability of medical records. Further, records in EHRS may be transferred electronically, thus reducing delays and errors in recording prescriptions or communicating laboratory test results.

Patient health information stored in EHR systems may be shared, with patient consent and in compliance with regulatory requirements, amongst healthcare professionals or between business units within the healthcare provider's organization using EHR systems. The sharing may be done through network-connected, enterprise-wide information systems or other information networks and exchanges that connect to EHR systems. As a result, one set of patient health information and records may be generated, maintained, and accessed by a plurality of individuals and systems, via EHR systems, resulting in healthcare providers being able to provide more streamlined and consistent care to patients.

Conventional EHR systems, however, have limitations. One limitation is that EHR systems often lacks user friendly graphical user interface (GUI) screens because these systems often require healthcare providers to flip through multiple screens to view all of the patient health information. For example, a patient's lab results may be viewed on one screen, a patient's x-rays or other medical images may be viewed on another screen, and patient billing and insurance information may be viewed on yet another screen. Thus, healthcare providers must flip through multiple screens to fully comprehend and obtain patient health information. This is cumbersome and inefficient when providing care to patients, especially in situations where certain health information is better viewed together (i.e., side-by-side) to aid in the healthcare provider's assessment of the patient's health or diagnosis.

Another limitation is the lack of customizability of EHR systems. EHR systems are software applications, and come with a predefined set of functionalities. That predefined set of functionalities may not meet the specific needs of certain healthcare providers.

Some EHR systems may have difficulty in exchanging data between healthcare providers that are using legacy systems and the EHR systems. Because different healthcare providers may use different legacy systems, each of which may have different data and file formats, to achieve widespread use and adoption, EHR systems have historically had to account for, and facilitate integration of, various systems and data formats, and ensure compatibility between data exchanged between these systems. This is cumbersome to implement and complex to manage.

To improve data exchange between legacy systems and EHR systems, standards have been developed to facilitate this data exchange. These standards include the Fast Healthcare Interoperability Resources (FHIR) standard.

The FHIR standard is a healthcare data exchange standard describing and defining data formats for exchanging electronic health records. The goal of FHIR is to facilitate interoperation between legacy healthcare systems and EHR systems, and to make it easy to provide health care information to healthcare providers and individuals on a wide variety of devices from computers to tablets to cell phones, and to allow third-party application developers to provide custom software applications to supplement the functioning of EHR systems, and to allow the custom software applications to easily integrated into existing systems. FHIR provides the standard data formats by which to do this.

SMART on FHIR is a technology built using the FHIR standard, and allows third-party application developers to use FHIR data formats to write software applications, using the SMART on FHIR API, to allow the custom software applications to integrate with EHR systems and exchange data between the custom software applications and EHR systems. Using SMART on FHIR as the underlying protocol, custom software applications may be integrated with any EHR systems compatible with SMART on FHIR to exchange data. Today's leading EHR systems support SMART on FHIR technology, which is built into the EHR systems. With the use of FHIR and SMART on FHIR, custom software applications may be integrated with or interfaced with an EHR system to facilitate data exchange between the software applications, the EHR system, and/or other systems.

However, a need still remains for a user friendly platform to populate relevant custom software applications for healthcare providers while they use EHR systems.

Systems and methods are needed to address these issues.

SUMMARY

Embodiments of this disclosure are directed to systems and methods of integrating a workflow platform with an EHR system. For brevity the EHR system will be referred to as an "EHRS" throughout this application. The system and methods disclosed provide a system and method that allows: (1) access to patient health information on a single screen, (2) the ability to update patient health information via the workflow platform and the ability to update the EHRS with the updated patient health information, and (3) a platform on which customized data and software applications may be built on, to extend the functionality of the EHRS.

Some embodiments are directed to systems and methods that at least receive from EHRS, a context tag embedded in a screen of the EHRS that is currently being presented to a user. The context tag includes at least: an authentication parameter identifying the user accessing the screen, and a context identification parameter identifying a context of the screen. Authentication may be performed to authenticate the user based on the authentication parameter. Based on authenticating the user, launch of a workflow platform may be initiated. The workflow platform can then be populated with data retrieved based on the context identification parameter such that which data is retrieved depends on the context identification parameter.

Certain embodiments of the disclosure have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

The accompanying drawings, which are incorporated herein and form a part of the specification, illustrate embodiments of the present disclosure and, together with the description, further serve to explain the principles of the disclosure and to enable a person skilled in the art to make and use the embodiments.

In the drawings, like reference numbers generally indicate identical or similar elements. Additionally, generally, the left-most digit(s) of a reference number identifies the drawing in which the reference number first appears.

DETAILED DESCRIPTION

Figure 1:
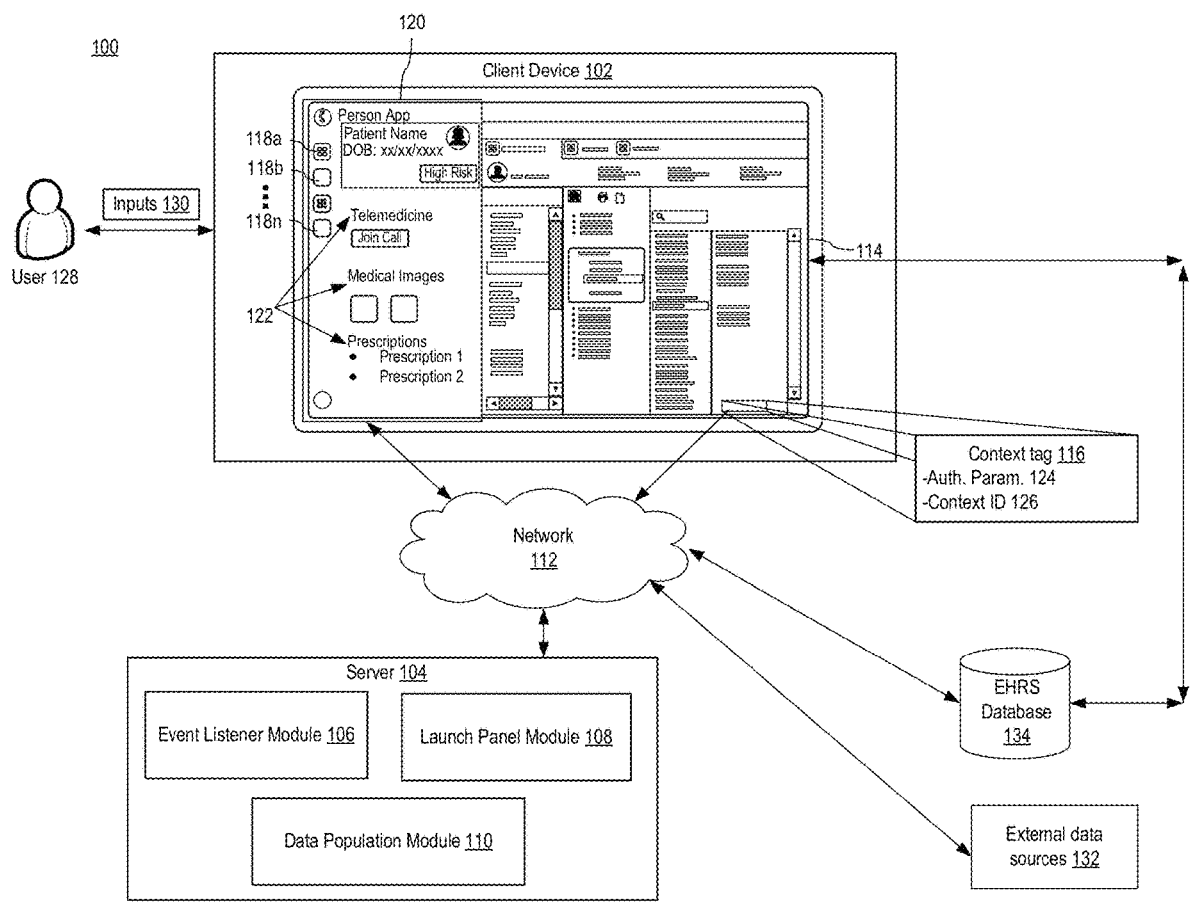
FIG. 1 is an example system for integrating a workflow platform with an EHRS according to embodiments.

The following embodiments are described in sufficient detail to enable those skilled in the art to make and use the disclosure. It is to be understood that other embodiments are evident based on the present disclosure, and that system, process, or mechanical changes may be made without departing from the scope of an embodiment of the present disclosure.

In the following description, numerous specific details are given to provide a thorough understanding of embodiments. However, it will be apparent that embodiments may be practiced without these specific details. To avoid obscuring an embodiment, some well-known circuits, system configurations, and process steps are not disclosed in detail.

The drawings showing embodiments of the system are semi-diagrammatic, and not to scale. Some of the dimensions are for the clarity of presentation and are shown exaggerated in the drawing figures. Similarly, although the views in the drawings are for ease of description and generally show similar orientations, this depiction in the figures is arbitrary for the most part. Generally, the system may be operated in any orientation.

Certain embodiments have other steps or elements in addition to or in place of those mentioned. The steps or elements will become apparent to those skilled in the art from a reading of the following detailed description when taken with reference to the accompanying drawings.

System Overview and Function

FIG. 1 illustrates an example system 100 for integrating a workflow platform 120 with an EHRS 114 according to embodiments. For the purposes of this disclosure, the EHRS 114 discussed is a standard health record system used to store and share patient health information. Such systems are known in the art. Examples of an EHRS 114 that may be used with the system 100 include the EPIC, CERNER, CARECLOUD, ATHENAHEALTH, GE CENTRICITY, and ALLSCRIPTS electronic health record systems.

The EHRS 114 may have a number of different components that can vary from vendor to vendor and from setting to setting. For example, the EHRS 114 in which embodiments of the present disclosure may be used may also include: (1) an electronic prescription (eRx) component 404, (2) a clinical and radiology laboratory component 406, (3) a transfer of care component 408, (4) a scheduling component 410, (5) a billing service component 412, and (6) a patient portal component 416. These will be described in greater detail below with respect to FIG. 4.

The workflow platform 120 is a software application sidebar or panel that is used in conjunction with the EHRS 114, but which is a separate software application. The workflow platform 120 has several features. A first feature is to consolidate patient health information found on different GUI screens of the EHRS 114, and present the patient health information in a streamlined and consolidated manner.

An important aspect of workflow platform 120 is its ability to identify, populate, and present the patient health information that is relevant to a context of a screen of the EHRS 114 being presented to a user 128. The user 128 may be, for example, a healthcare professional such as a doctor, nurse, clinician, billing specialist, etc. Context refers to what topics relate to the screen currently being presented to the user 128. Workflow platform 120 can identify, populate, and present this information relevant to the EHRS 114 in a separate application. Thus, the system 100 is unique in that it can identify, and the workflow platform 120 can present, patient health information relevant to topics related to a screen currently shown to user 128. How the system 100 identifies the context of the screen being presented by the EHRS 114 will be discussed further below.

By way of example, if the user 128 is presented a screen showing a patient's insurance information, the system 100 can identify the context to be that the user 128 is viewing billing or financial related information, and further populate the workflow platform 120 with patient health information relevant to billing or financial related information for the patient, that the workflow platform 120 can display in data fields 122. This may be, for example, information such as the patient's billing address, links to patient billing statements, links to patient explanation of benefits statements, outstanding balances, links to or contact information for the patient's insurance provider, etc.

As another example, if the user 128 is presented a screen showing a patient's lab work, the system 100 can identify the context to be that the user 128 is viewing a patient's health records, and further populate the workflow platform 120 with patient health information relevant to a patient's health records, that the workflow platform 120 can display in data fields 122. This may be, for example, patient medical charts, medical images, a list of medications the patient is taking, etc. The aforementioned is merely exemplary and not meant to be limiting.

Data fields 122 are areas or panels of the workflow platform 120 that present information. The data fields 122 may be populated with patient health information by the system 100 with data obtained from the EHRS 114, via, for example an EHRS database 134 storing the patient health information, or from external data sources 132 external to the EHRS 114 from which the patient health information can also be obtained. The external data sources 132 may be corporations, laboratories, clinics, databases, repositories, etc., as examples, that are integrated with the system 100. In one embodiment, the integration may be via application programming interfaces (APIs). For example, the external data sources 132 may implement software applications using the SMART on FHIR API to facilitate transfer of patient health information.

A second feature of the workflow platform 120 is to allow the user 128 the ability to provide one or more inputs 130 to update a patient health record on the EHRS 114. The inputs 130 can represent updates to patient health information. The inputs 130 may be, for example, updates to the patient medical records based on a doctor visit, updates based on lab results, updates based on changes in billing information, etc. The workflow platform 120 can facilitate updating the ERRS 114 with the inputs 130 by transmitting the inputs 130 to a server 104, which can update a patient health record based on the inputs 130. In one embodiment, the server 104 can update the EHRS database 134 to update the patient health record. In one embodiment, the ERRS 114 is updated in real-time. Real-time refers to updating the patient health records on the EHRS 114 near instantaneously from when the workflow platform 120 receives the inputs 130.

A third feature of the workflow platform 120 is to serve as a platform on which customized software applications 118 are populated, to be used by the user 128 to extend the functionality of the ERRS 114. The customized software applications 118 refer to custom software that may be integrated with the workflow platform 120, and launched via the workflow platform 120 through icons or buttons displayed on the workflow platform 120. When the icons or buttons are clicked or initiated by the user 128, the customized software applications 118 may be executed to provide some functionality. In FIG. 1, the icons or buttons for the customized software applications 118 are shown as {118a, 118b, . . . 118n}.

The customized software applications 118 may be thought of as analogous to mobile phone applications used on mobile phones. The analogy, however, does not imply that the customized software applications 118 must be used on mobile devices, but just that they may be discrete and custom software that may be used on a device to provide some specific functionality. The workflow platform 120 enables the use of the customized software applications 118. In one embodiment, the customized software applications 118 can implement SMART on FHIR API to integrate with the workflow platform 120 and/or the EHRS 114. The workflow platform 120 provides the interface by which to access the customized software applications 118.

As indicated, in one embodiment, the customized software applications 118 may be used to extend the functionality of the EHRS 114 by allowing custom software to be built providing some functionality that the ERRS 114 may lack. Example functionalities include allowing for telemedicine or video conferencing capabilities via the workflow platform 120, or providing custom built analytics tools that access the patient health information from the EHRS 114 or external data sources 132, to allow the user 128 to perform analytics based on the patient health information. The aforementioned are merely exemplary and not meant to be limiting.

In one embodiment, the workflow platform 120 and the EHRS 114 may be implemented on a client device 102, which is coupled to a server 104 via a network 112. The server 104 functions as an intermediary between the workflow platform 120 and the EHRS 114 to exchange patient health information between the two. For example, the workflow platform 120 can provide patient health information to the user 128 provided from the ERRS 114 and/or the EHRS database 134, via the server 104. The workflow platform 120 can also allow the user 128 to provide the inputs 130 to the EHRS 114, via the server 104. The server 104 also functions to synchronize data between the workflow platform 120 and the EHRS 114 and/or the EHRS database 134. For example, the server 104 can update the patient health information on the EHRS database 134 based on the inputs 130 provided by the user 128 via the workflow platform 120.

In one embodiment, the client device 102, the server 104, or a combination thereof can enable some or all of the functionality of the EHRS 114 and the workflow platform 120. For example, in one embodiment, the software implementing the workflow platform 120 may be installed on the client device 102 as instructions on a non-transitory computer readable medium, for example as a desktop application. The client device 102 can execute the instructions to implement the functionality of the workflow platform 120. In another embodiment, both the client device 102 and the server 104 can have portions of the software implementing the workflow platform 120 installed as instructions on a non-transitory computer readable medium. The client device 102 and the server 104 can both execute portions of the software to implement the functionality of the workflow platform 120 using client-server architectures known in the art. Similarly, in one embodiment, the client device 102, the server 104, or a combination thereof can execute some or all of the software implementing the EHRS 114.

The client device 102 may be any of a variety of centralized or decentralized computing devices. For example, the client device 102 may be a mobile device, a laptop computer, or a desktop computer, as examples. While the client device 102 can couple with the network 112 to communicate with the server 104, the client device 102 can also function as a stand-alone device separate from the server 104. Stand-alone refers to a device being able to work and operate independently of other devices.

The server 104 can also be a variety of centralized or decentralized computing devices. For example, the server 104 may be a mobile device, a laptop computer, a desktop computer, grid-computing resources, a virtualized computing resource, cloud computing resources, peer-to-peer distributed computing devices, a server farm, or a combination thereof. The server 104 may be centralized in a single room, distributed across different rooms, distributed across different geographical locations, or embedded within the network 112. While the server 104 can couple with the network 112 to communicate with the client device 102, the server 104 can also function as a stand-alone device separate from the client device 102.

The network 112 refers to a telecommunications network, such as a wired or wireless network. The network 112 can span and represent a variety of networks and network topologies. For example, the network 112 can include wireless communication, wired communication, optical communication, ultrasonic communication, or a combination thereof. For example, satellite communication, cellular communication, Bluetooth, Infrared Data Association standard (IrDA), wireless fidelity (WiFi), and worldwide interoperability for microwave access (WiMAX) are examples of wireless communication that may be included in the network 112. Cable, Ethernet, digital subscriber line (DSL), fiber optic lines, fiber to the home (FTTH), and plain old telephone service (POTS) are examples of wired communication that may be included in the network 112. Further, the network 112 can traverse a number of topologies and distances. For example, the network 112 can include a direct connection, personal area network (PAN), local area network (LAN), metropolitan area network (MAN), wide area network (WAN), or a combination thereof. For illustrative purposes, in the embodiment of FIG. 1, the system 100 is shown with the client device 102 and the server 104 as end points of the network 112. This, however, is exemplary and it is understood that the system 100 can have a different partition between the client device 102, the server 104, and the network 112. For example, the client device 102 and the server 104 can also function as part of the network 112.

In one embodiment, the server 104 can further include modules to perform some or all of the functionality of the system 100. The modules can include, at least, an event listener module 106, a launch panel module 108, and a data population module 110. The modules, and how they facilitate the interactions between the workflow platform 120 and the EHRS 114 will be discussed further below. While FIG. 1 shows the modules being on the server 104, this is merely exemplary and for ease of description. In other embodiments, some or all of the modules may be on other devices of the system 100, for example on the client device 102.

As shown in FIG. 1, in one embodiment, the workflow platform 120 and the EHRS 114 may be operated side-by-side on the client device 102. In one embodiment, the workflow platform 120 may be launched (i.e., opened) on the client device 102, and populated with patient health information via the server 104 based on a signal transmitted from the EHRS 114 to the server 104.

In one embodiment, the signal can take the form of a context tag 116 transmitted by the EHRS 114 to the server 104. The context tag 116 may be a hyperlink embedded with data, a data structure, a tracking pixel embedded in a screen of the EHRS 114, or a combination thereof. In one embodiment, the server 104, upon receipt of the context tag 116 from the EHRS 114 can initiate launch of the workflow platform 120 by, for example, generating and transmitting a signal to the client device 102 instructing the client device 102 to execute the instructions to launch the workflow platform 120. Once launched, the workflow platform 120 may be populated with patient health information based on the context of the screen of the EHRS 114 currently being presented to the user 128. Details regarding the launching of workflow platform 120 and its population with data will be discussed further below.

In one embodiment, the context tag 116 can include one or more variables or parameters. Based on the variables or parameters, the launching of the workflow platform 120 and the population of the patient health information are performed. In one embodiment, the variables or parameters can include at least an authentication parameter 124 and a context identification parameter 126. The authentication parameter 124 refers to a variable or parameter used to identify and authenticate the user 128. The context tag 116 is used to identify the context of the screen currently being presented to the user 128. How the authentication parameter 124 and the context identification parameter 126 are used will be discussed further below.

Figure 2:
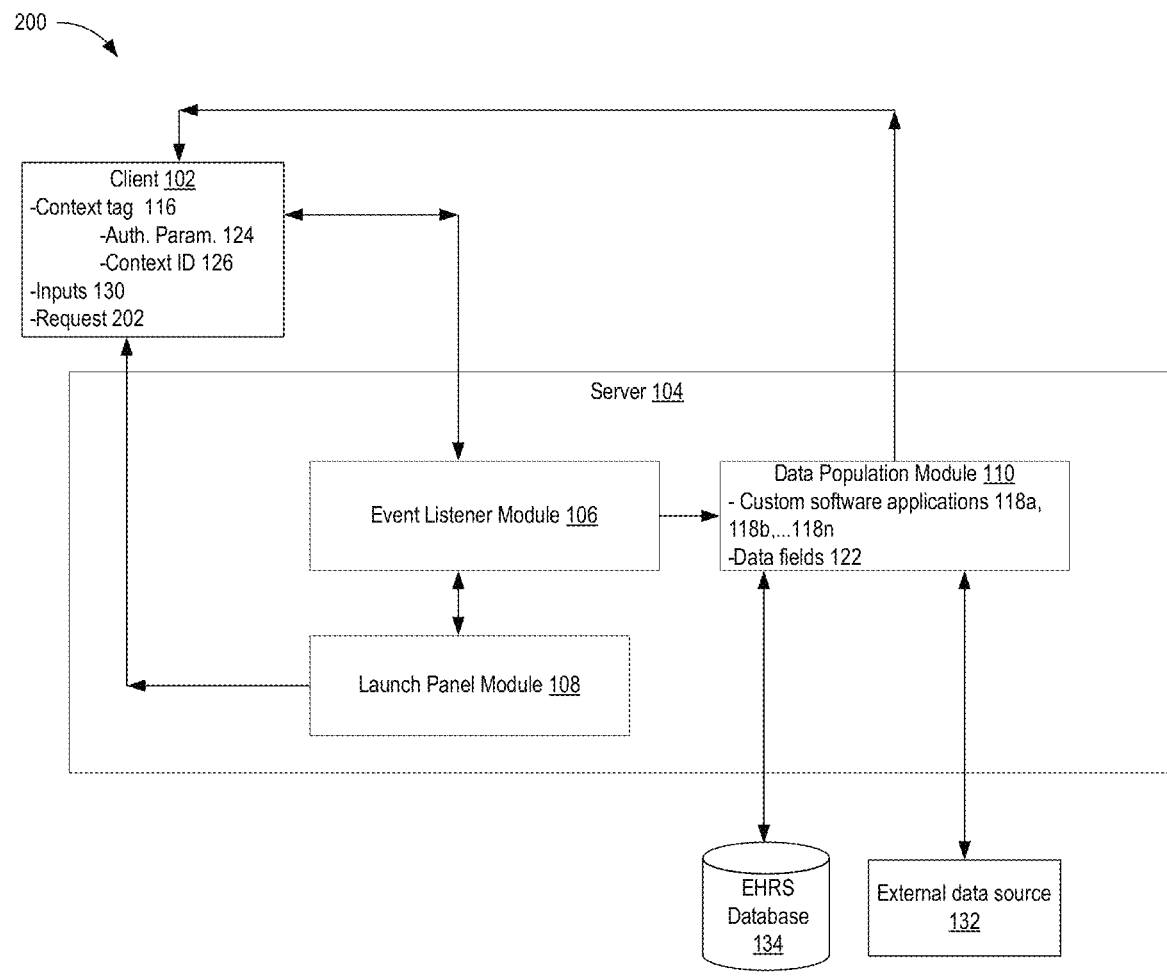
FIG. 2 is an example control flow for the system according to embodiments.

FIG. 2 shows an example control flow 200 for the system 100 according to embodiments. The control flow 200 includes the event listener module 106, the launch panel module 108, and the data population module 110. In one embodiment, the event listener module 106 can couple to the client device 102. The event listener module 106 can further couple to the launch panel module 108 and the data population module 110. The launch panel module 108 can couple to the client device 102. The data population module 110 can also couple to the client device 102, the EHRS database 134, and the external data sources 132.

In one embodiment, the control flow 200 may begin with the context tag 116 being transmitted, via the network 112, from the EHRS 114 to the event listener module 106. The event listener module 106 enables receipt of the context tag 116. As indicated with respect to FIG. 1, the context tag 116 may include a hyperlink embedded with data, a data structure, a tracking pixel embedded in a screen of the EHRS 114, or a combination thereof.

For the purposes of discussion with respect to FIG. 2, it is assumed that the context tag 116 is a tracking pixel embedded in each screen of the EHRS 114. A tracking pixel refers to a software code embedded within a screen of the EHRS 114 as a graphic with dimensions of a 1×1 pixel on each screen of the EHRS 114. Tracking pixels and how they are used is known in the art. For the purposes of FIG. 2, it is assumed that the context tag 116 is implemented as a tracking pixel embedded on each screen of the EHRS 114.

In one embodiment, the tracking pixel may be embedded on each screen of the EHRS 114 using SMART on FHIR technology. As previously indicated, SMART on FHIR is typically built into EHR systems, and allows integration of the EHRS 114 with third-party applications, for example the customized software applications 118. By way of example, if a third-party application is to, for example, integrate a physician's MICROSOFT OUTLOOK calendar into the EHRS 114, a developer can build a component, and using SMART on FHIR technology, integrate the component to MICROSOFT OUTLOOK, using the MICROSOFT OUTLOOK API and the SMART on FHIR API. The SMART on FHIR API can allow the component to embed the physician's MICROSOFT OUTLOOK calendar into a frame of the EHRS 114. A frame refers to a portion of one or more of the screens of the EHRS 114 where a graphic may be displayed. Thus, the physician's MICROSOFT OUTLOOK calendar may be displayed in the frame. In order to see the physician's calendar, this component can submit a request to a server associated with the calendar. The request would have authentication information and/or context information that may be used to authenticate the EHRS 114 or a user 128. Based on authenticating the EHRS 114, the physician's calendar may be pushed back to the EHRS 114 and displayed within the frame.

However, aspects of this disclosure take this functionality provided by SMART on FHIR, and, instead of using it to generate a frame within the EHRS 114, use it to populate data and the customized software applications 118 to the workflow platform 120. This is done by using SMART on FHIR to embed the tracking pixel within a frame of the EHRS 114. The tracking pixel can then be used to pass authentication and context information of the screen of the EHRS 114 to the server 104 and based on the same, the server 104 can populate the workflow platform 120 with data and the customized software application 118 it retrieves from the EHRS database 134 or external data sources 132. In this way, embodiments take an existing functionality provided by SMART on FHIR, and use it for a new purpose, which is to push data and customized software applications 118 to the workflow platform 120. In embodiments, the context tag 116 may be transmitted to the server 104 automatically or non-automatically. Further details regarding the automatic and non-automatic transmission of the context tag 116 will be discussed further below.

Continuing with the example, in one embodiment, the context tag 116 enables the authentication of the user 128 and identification of the context of the screen being accessed by the user 128. In order to enable these functions, the context tag 116 includes at least the authentication parameter 124 and the context identification parameter 126.

In one embodiment, the authentication parameter 124 may be, for example, a username and password pair, that is used to identify and authenticate the user 128. In another embodiment, the authentication parameter 124 may be a code or identifier of the ERRS 114. For example, in one embodiment, and if the authentication parameter 124 is a username and password pair, the authentication parameter 124 may be obtained from a login screen of the EHRS 114 that the user 128 logs into. The login information can include the username and password pair which is saved as the authentication parameter 124. In one embodiment, the authentication parameter 124 may be encoded into the context tag 116 of each screen of the EHRS 114 once the user 128 logs into the EHRS 114 to access patient health information.

Continuing with the example, in one embodiment, the event listener module 106 can use the authentication parameter 124 to authenticate the user 128. The purpose of the authentication is to ensure a user 128 is authorized to view the patient health information and the data to be populated into the workflow platform 120 based on the context of the screen. The event listener module 106 can perform the authentication using any known authentication techniques. For example, in one embodiment, and in the most basic form of authentication, assuming the authentication parameter 124 is a username and password pair for the user 128, the event listener module 106 can compare the authentication parameter 124 to username and password pairs stored on a database, such as the EHRS database 134, to verify that the user 128 accessing the screen is authorized to view the screen. If a match is found such that the authentication parameter 124 is matched to an account identifying that the user 128 is credentialed to view the patient health information, the event listener module 106 can determine that the user 128 is authorized to view the patient health information. A similar mechanism may be used if a code or identifier of the EHRS 114 is used as the authentication parameter 124.

In one embodiment, based on performing the authentication, the event listener module 106 can generate a signal to the launch panel module 108 to initiate launch of the workflow platform 120. The signal may be a variable, parameter, or data structure, as examples. In one embodiment, upon receipt of the signal, the launch panel module 108 can execute code that launches the workflow platform 120. This may be done, for example, by executing software code or a script to open the workflow platform 120 on the client device 102. In one embodiment, once the workflow platform 120 is launched on the client device 102, the launch panel module 108 can generate a further signal, and transmit the further signal to the event listener module 106 indicating successful launch of the workflow platform 120 on the client device 102. Upon receipt of the further signal, the event listener module 106 can pass control and the context tag 116 to the data population module 110.

The data population module 110 enables the identification of the context of the EHRS 114 screen that is being presented to the user 128, and further enables population of data, including patient health information into the workflow platform 120, based on the identification of the context. In order to identify the context of the screen, the data population module 110 utilizes the context identification parameter 126. For the purposes of this disclosure, it is assumed that each GUI screen of the EHRS 114 is encoded with a context identification parameter 126 used to identify the context of the screen. In one embodiment, the context identification parameter 126 may be an alpha-numeric code or number that is used to identify the context of the screen. For example, the alpha-numeric code or number may be a medical record number for a patient, a claim identification number for a patient, an order identification number for a patient, etc. embedded into the screen as the context identification parameter 126. What alpha-numeric code or number is used as the context identification parameter 126 may be determined by a developer or administrator of the system 100 as part of the setup process of the EHRS 114 or system 100. In this way, each screen has a context identification parameter 126 in advance of being presented to the user 128.

Continuing with the example, in one embodiment, based on the alpha-numeric code or number used for the context identification parameter 126, the data population module 110 can identify the context of each screen. In one embodiment, this may be done by comparing the context identification parameter 126 to a set of known alpha-numeric codes or numbers mapped to various pre-defined topics, and stored on a database or repository. The topics refer to pre-defined themes or concepts that are used to group patient health information stored on the EHRS 114 and/or the EHRS database 134. The topics may be classifications, which may be used to group patient health information. In one embodiment, each piece of patient health information can have an associated topic associated with it such that it may be categorized under a certain topic or a set of topics.

For example, and by way of example, a patient lab result may be associated with the topic "LAB RESULT" or "PATIENT HEALTH RECORD", a patient insurance information may be associated with the topic "PATIENT BILLING", etc. Thus, each piece of health information may be mapped to a topic. In one embodiment, the topics may be pre-defined by a developer or administrator of the system 100. Thus, because each context identification parameter 126 has an associated topic or set of topics, the data population module 110 can determine what the context of the screen is by knowing what topics the screen relates to.

In one embodiment, once the data population module 110 identifies the context of the screen, the data population module 110 can access the relevant patient health information mapped to that topic and retrieve it from data sources to populate the workflow platform 120 with the relevant patient health information associated with that topic. These data sources may be the EHRS database 134, the external data sources 132, or a combination thereof. Once retrieved by the data population module 110, the patient health information may be populated into the data fields 122 of the workflow platform 120.

In one embodiment, the data population module 110 can further populate the workflow platform 120 with the customized software applications 118. The customized software applications 118, similar to the patient health information, can also be mapped to topics and the context identification parameter 126. For example, in one embodiment, each custom software application 118 may be categorized based on its functionality, to relate to a specific topic. For example, if the customized software applications 118 relate to patient billing or provide communication capabilities to a patient's insurance company, they may be mapped to the topic "PATIENT BILLING". In another example, if the customized software applications 118 relate to the ability to do analytics based on patient lab results, they may be mapped to the topic "LAB RESULT" or "PATIENT HEALTH RECORD". The aforementioned are merely exemplary and not meant to be limiting as to what the customized software applications 118 or their mappings to topics may be. In this way, the data population module 110 can populate the customized software application 118 onto the workflow platform 120 based on the context identification parameter 126 in a similar manner as how it populates the patient health information. Once populated onto the workflow platform by the data population module 110, the patient health information, the customized software applications 118, or a combination thereof may be viewed and/or used by the user 128.

As mentioned with respect to FIG. 1, in one embodiment, the user 128 can further interact with the EHRS 114 via the workflow platform 120. This interaction may be, for example, providing the inputs 130. In one embodiment, the user 128 can provide the inputs 130 into the workflow platform 120 via interactive panels, boxes, buttons, graphics, etc., as examples. In one embodiment, the workflow platform 120 can transmit the inputs 130 to the event listener module 130. The event listener module 130, upon receipt of the inputs 130 can further pass the inputs 130 to the data population module 110. In one embodiment, the data population module 110 can enable the updating of the EHRS 114 and/or the EHRS database 132 with the inputs 130 as described with respect to FIG. 1. This may be done, for example, by further transmitting the inputs 130 to the EHRS database 134 to update the health record of the patient with these updates. By way of example, if the user 128 is a doctor who inputs notes into the workflow platform 120 after or during a patient visit, the workflow platform 120 can transmit the notes to the event listener module 106, which can further transmit the notes to the data population module 110, which can then update the EHRS database 134 with the notes. The data population module 110 can perform the updating by, for example, interfacing with the EHRS database 134 via an API to transmit the updates to the EHRS database 134. Similarly, in one embodiment, the data population module 110 can send the updates to external data sources 132 in a similar manner.

In one embodiment, the aforementioned control flow 200 may be performed by the modules automatically upon receiving the context tag 116 from the EHRS 114. Automatically refers to the control flow 200 being performed without any user 128 intervention or control. Thus, upon receipt of the context tag 116 the authentication of the user 128, initiating launch of the workflow platform 120, and the identification of the context of a screen of the EHRS 114 may be done without any user 128 intervention or control. In the embodiment where control flow 200 is performed automatically, the context tag 116 is transmitted from the EHRS 114 upon the presentation of the screen of the EHRS 114 to the user 128.

In another embodiment, the aforementioned control flow 200 may be performed by the modules non-automatically. Non-automatically refers to the control flow 200 being performed with user 128 intervention or control. In the embodiment, where the control flow 200 is performed in a non-automatic manner, the user 128 can provide a user request 202 requesting the control flow 200 to be initiated. This may be done, for example, by the user 128 providing the user request 202, via a button or icon on the EHRS 114 screen, implemented in a frame on the screen of the EHRS 114 that also contains the context tag 116. In one embodiment, when the button or icon is clicked on or triggered by the user 128 the clicking results in the transmission of the context tag 116 from the EHRS 114 to the event listener module 106.

The modules described in FIGS. 1 and 2 may be implemented as instructions stored on a non-transitory computer readable medium to be executed by one or more computing units such as a processor, a special purpose computer, an integrated circuit, integrated circuit cores, or a combination thereof. The non-transitory computer readable medium may be implemented with any number of memory units, such as a volatile memory, a nonvolatile memory, an internal memory, an external memory, or a combination thereof. The non-transitory computer readable medium may be integrated as a part of the system 100 or installed as a removable portion of the system 100.

It has been discovered that the system 100 described above significantly improves the state of the art from previous systems because it provides a way for healthcare providers to access patient health information quickly and on a single interface without having to search for the data by navigating through multiple GUI screens of the EHRS 114. This is achieved through the use of the workflow platform 120, which is populated with patient health information found on different screens of the EHRS 114. In addition to the ability to consolidate patient health information, the system 100 is unique in that it can identify the context of each screen of the EHRS 114, through the use of the context tag 116. By identifying the context of each screen, the system 100 can further streamline the data presented via the workflow platform 120 by providing only relevant patient healthcare information related to the context of the screen. In this way, the healthcare provider may be provided with only the necessary and relevant patient health information based on the context of each screen that is presented.

It has been further discovered that the consolidation and presentation of the patient health care information by the system 100 further increases the speed and efficiency by which the healthcare provider can provide services to the patient, by saving the healthcare provider time from having to search for patient health information on the EHRS 114.

It has been further discovered that the system 100 improves the art by providing the ability to update patient health information via the workflow platform 120 and the ability to update the EHRS 114 with the updated patient health information, particularly in real-time. Current EHR systems do not allow this ability to update patient health information in real-time and often update patient health records as a batch process. The batch processes may update the information, for example, once a day. The system 100, by connecting to the EHRS 114 and/or the EHRS database 134, can push updates to the EHRS 114 in real-time. This allows for the most up to date information being on the EHRS 114. This further allows healthcare providers to see the most up to date patient health records, allowing them to provide better care for patients.

It has been further discovered that the system 100 improves the art by facilitating and providing a platform on which customized software applications 118 may be built on and shared with healthcare providers in a targeted manner, to extend the functionality of EHRS 114. By providing targeted customized software applications 118 to healthcare providers, the system 100 allows for the extension of the EHRS 114 functionality while allowing only the most relevant customized software application 118 to be used by the healthcare providers to provide care for patients. This greatly improves the usability of EHRS 114 and the ability of healthcare providers to provide better care to patients.

Methods of Operation

Figure 3:
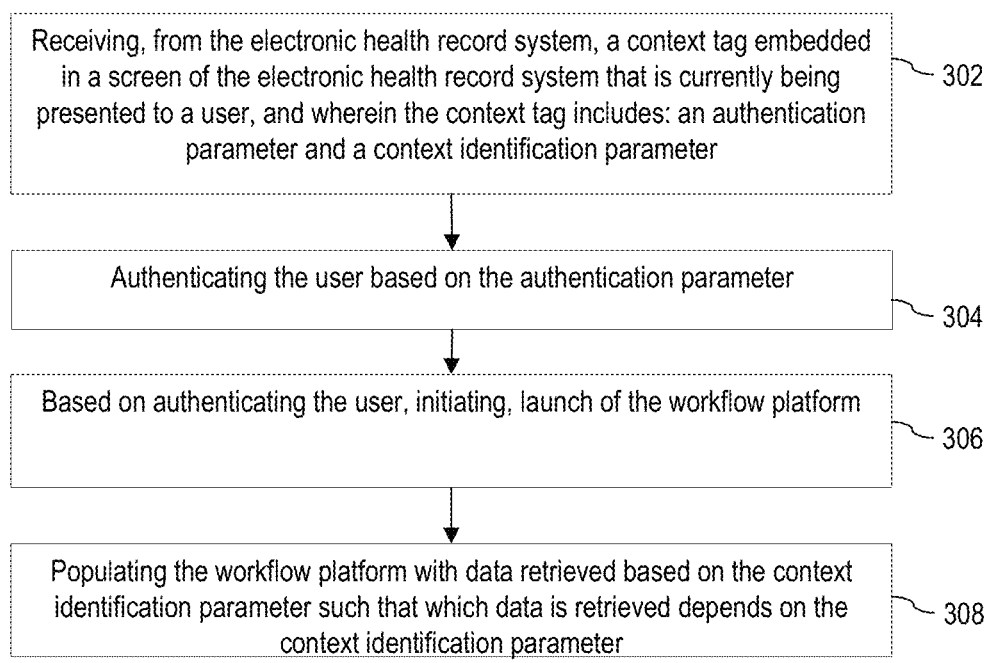
FIG. 3 is an example method of operating the system according to embodiments.

FIG. 3 shows example method 300 of operating the system 100 according to embodiments.

The method 300 includes receiving, by one or more computing devices and from the EHRS 114, a context tag 116 embedded in a screen of the EHRS 114 that is currently being presented to a user 128, where the context tag 116 includes: an authentication parameter 124 identifying the user 128 accessing the screen, and a context identification parameter 126 identifying a context of the screen, as shown in 302.

The method 300 further includes authenticating, by the one or more computing devices, the user 128 based on the authentication parameter 126, as shown in 304. Authenticating may be done as described with respect to FIG. 2, by for example, comparing the authentication parameter 124 to known usernames, passwords, or other authentication codes, that are linked to accounts authorized to access patient health information.

Based on authenticating the user 128, the method 300 initiates, by the one or more computing devices, launch of the workflow platform 120, as shown in 306. For example, and as described with respect to FIG. 2, based on comparing the authentication parameter 124 to known usernames, passwords, or other authentication codes, that are linked to accounts authorized to access patient health information, if a match is found such that the authentication parameter 124 is matched to an account identifying a credentialed user 128 credentialed to view the patient health information, the event listener module 106 can determine that the user 128 is authorized to view the patient health information.

The method 300 further includes populating, by the one or more computing devices, the workflow platform 120 with data retrieved based on the context identification parameter 126, such that which data is retrieved depends on the context identification parameter 126, as shown in 308. For example, and as described with respect to FIG. 2, the data population module 110 can utilize the context identification parameter 126 to populate the workflow platform 120 with data retrieved, by matching the context identification parameter 126 with a set of known alpha-numeric codes or numbers mapped to various pre-defined topics, and stored on a database or repository. Based on the alpha-numeric codes or number the context identification parameter 126 is matched to, the data population module 110 can populate the workflow platform 120 to with data mapped to those topics.

The operation of method 300 is performed, for example, by system 100, in accordance with embodiments described above. In embodiments, the method 300 may be performed automatically or non-automatically, as described with respect to FIG. 2. For example, method 300 may be performed automatically when a screen of the EHRS 114 is presented to the user 128. Alternatively, method 300 may be performed non-automatically if a user 128 provides a user request 202 by way of pressing a button or icon in a frame of the EHRS 114 to trigger the transmission of the context tag 116 to the server 104.

Components of the System

Figure 4:
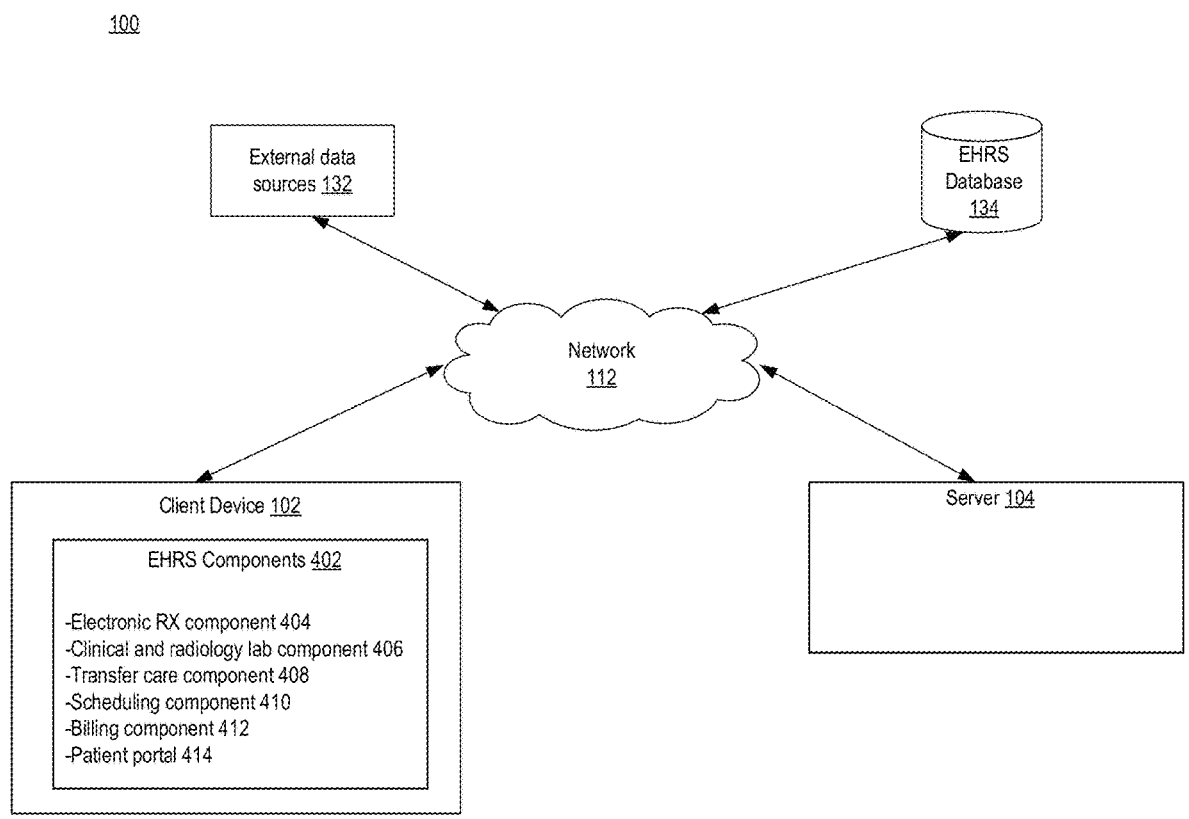
FIG. 4 shows example components of the EHRS according to embodiments.

FIG. 4 shows example components 402 of the EHRS 114 according to embodiments. As described above, the EHRS 114 may include: (1) an electronic prescription (eRx) component 404, (2) a clinical and radiology laboratory component 406, (3) a transfer of care component 408, (4) a scheduling component 410, (5) a billing service component 412, and (6) a patient portal component 414. In one embodiment, the aforementioned components may be part of the software installed on the client device 102, as for example a desktop application.

The electronic prescription component 404 provides medical professionals capabilities to electronically generate and transmit prescriptions for patient's medications. In one embodiment, EHRS 114 may enable prescribers to view their patient's prescription benefit information at the point of care and select medications that are on formulary and covered by the patient's drug benefit. This informs physicians of potential lower cost alternatives (such as generic drugs) and reduces administrative burden of pharmacy staff and physicians related to benefit coverage.

The clinical and radiology laboratory component 406 allows medical professionals to integrate with clinical laboratories to electronically receive and incorporate clinical laboratory tests and results into a patient's chart and create computerized provider order entry (CPOE) clinical laboratory orders. This component can also support functionality that enables medical professionals to electronically receive and incorporate radiology laboratory test results (e.g., x-ray, ultrasound, MRI, PET/CT scan, mammography) into a patient's chart.

Medical professionals can use the transfer of care component 408 to transmit referrals electronically to other EHR users or to non-users by facsimile. Additionally, EHRS 114 may support electronically creating and transmitting consolidated continuity of care documents.

The scheduling component 410 offers functionality that allows healthcare providers to manage their appointments with an electronic schedule that may be integrated into a practice's workflow.

The billing service component 412 offers healthcare professionals the ability to electronically generate and transmit superbills. Superbills are the data source for the creation of a healthcare claim. The billing service component can transmit superbills to medical billing software accounts controlled by the professionals' offices or their billing service providers. This component also allows a healthcare professional to save a superbill and transmit it to the health care professional's billing account with the billing software vendor.

The patient portal component allows medical professionals to grant their patients an online means to view, download, and transmit their health information, often called the personal health record (PHR). This component also provides patients with the ability to review their physicians and send and receive secure messages directly to and from their physicians.

Figure 5:
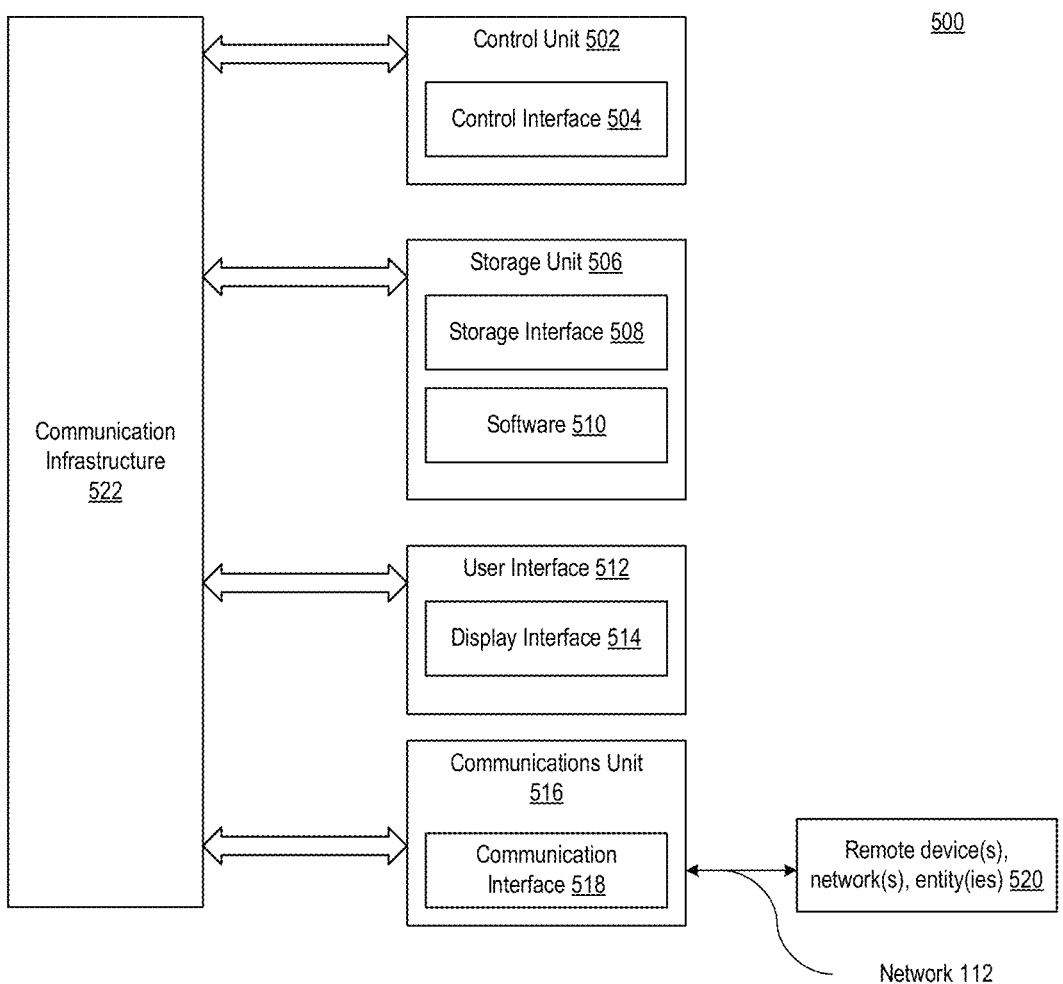
FIG. 5 is an example architecture of the components implementing the system according to embodiments.

FIG. 5 shows an example architecture 500 of the components implementing the system 100 according to embodiments. In one embodiment, the components may include a control unit 502, a storage unit 506, a communication unit 516, and a user interface 512. The control unit 502 may include a control interface 504. The control unit 502 may execute a software 510 to provide some or all of the intelligence of system 100. The control unit 502 may be implemented in a number of different ways. For example, the control unit 502 may be a processor, an application specific integrated circuit (ASIC), an embedded processor, a microprocessor, a hardware control logic, a hardware finite state machine (FSM), a digital signal processor (DSP), a field programmable gate array (FPGA), or a combination thereof.

The control interface 504 may be used for communication between the control unit 502 and other functional units or devices of system 100. The control interface 504 may also be used for communication that is external to the functional units or devices of system 100. The control interface 504 may receive information from the functional units or devices of system 100, or from remote devices 520, such as the EHRS database 134 or the external data sources 132, or may transmit information to the functional units or devices of system 100, or to remote devices 520. The remote devices 520 refer to units or devices external to system 100.

The control interface 504 may be implemented in different ways and may include different implementations depending on which functional units or devices of system 100 or remote devices 520 are being interfaced with the control unit 502. For example, the control interface 504 may be implemented with a pressure sensor, an inertial sensor, a microelectromechanical system (MEMS), optical circuitry, waveguides, wireless circuitry, wireline circuitry to attach to a bus, an application programming interface, or a combination thereof. The control interface 504 may be connected to a communication infrastructure 522, such as a bus, to interface with the functional units or devices of system 100 or remote devices 520.

The storage unit 506 may store the software 510. For illustrative purposes, the storage unit 506 is shown as a single element, although it is understood that the storage unit 506 may be a distribution of storage elements. Also for illustrative purposes, the storage unit 506 is shown as a single hierarchy storage system, although it is understood that the storage unit 506 may be in a different configuration. For example, the storage unit 506 may be formed with different storage technologies forming a memory hierarchical system including different levels of caching, main memory, rotating media, or off-line storage. The storage unit 506 may be a volatile memory, a nonvolatile memory, an internal memory, an external memory, or a combination thereof. For example, the storage unit 506 may be a non-volatile storage such as nonvolatile random access memory (NVRAM), Flash memory, disk storage, or a volatile storage such as static random access memory (SRAM) or dynamic random access memory (DRAM).

The storage unit 506 may include a storage interface 508. The storage interface 508 may be used for communication between the storage unit 506 and other functional units or devices of system 100. The storage interface 508 may also be used for communication that is external to system 100. The storage interface 508 may receive information from the other functional units or devices of system 100 or from remote devices 520, or may transmit information to the other functional units or devices of system 100 or to remote devices 520. The storage interface 508 may include different implementations depending on which functional units or devices of system 100 or remote devices 520 are being interfaced with the storage unit 506. The storage interface 508 may be implemented with technologies and techniques similar to the implementation of the control interface 504.

The communication unit 516 may enable communication to devices, components, modules, or units of system 100 or to remote devices 520. For example, the communication unit 516 may permit the system 100 to communicate between its components the client device 102 and the server 104. The communication unit 516 may further permit the devices of system 100 to communicate with remote devices 520 such as an attachment, a peripheral device, or a combination thereof through the network 112.

As previously indicated, the network 112 may span and represent a variety of networks and network topologies. For example, the network 112 may be a part of a network and include wireless communication, wired communication, optical communication, ultrasonic communication, or a combination thereof. For example, satellite communication, cellular communication, Bluetooth, Infrared Data Association standard (IrDA), wireless fidelity (WiFi), and worldwide interoperability for microwave access (WiMAX) are examples of wireless communication that may be included in the network 112. Cable, Ethernet, digital subscriber line (DSL), fiber optic lines, fiber to the home (FTTH), and plain old telephone service (POTS) are examples of wired communication that may be included in the network 112. Further, the network 112 may traverse a number of network topologies and distances. For example, the network 112 may include direct connection, personal area network (PAN), local area network (LAN), metropolitan area network (MAN), wide area network (WAN), or a combination thereof.

The communication unit 516 may also function as a communication hub allowing system 100 to function as part of the network 112 and not be limited to be an end point or terminal unit to the network 112. The communication unit 516 may include active and passive components, such as microelectronics or an antenna, for interaction with the network 112.

The communication unit 516 may include a communication interface 518. The communication interface 518 may be used for communication between the communication unit 516 and other functional units or devices of system 100 or to remote devices 520. The communication interface 518 may receive information from the other functional units or devices of system 100, or from remote devices 520, or may transmit information to the other functional units or devices of the system 100 or to remote devices 520. The communication interface 518 may include different implementations depending on which functional units or devices are being interfaced with the communication unit 516. The communication interface 518 may be implemented with technologies and techniques similar to the implementation of the control interface 504.

The user interface 512 may present information generated by system 100. In one embodiment, the user interface 512 allows the user 128 to interface with the devices of system 100 or remote devices 520. The user interface 512 may include an input device and an output device. Examples of the input device of the user interface 512 may include a keypad, buttons, switches, touchpads, soft-keys, a keyboard, a mouse, or any combination thereof to provide data and communication inputs. Examples of the output device may include a display interface 514. The control unit 502 may operate the user interface 512 to present information generated by system 100. The control unit 502 may also execute the software 510 to present information generated by system 100, or to control other functional units of system 100. The display interface 514 may be any graphical user interface such as a display, a projector, a video screen, or any combination thereof.

The terms "module" or "unit" referred to in this disclosure can include software, hardware, or a combination thereof in an embodiment of the present disclosure in accordance with the context in which the term is used. For example, the software may be machine code, firmware, embedded code, or application software. Also for example, the hardware may be circuitry, a processor, a special purpose computer, an integrated circuit, integrated circuit cores, a pressure sensor, an inertial sensor, a microelectromechanical system (MEMS), passive devices, or a combination thereof. Further, if a module or unit is written in the system or apparatus claims section below, the module or unit is deemed to include hardware circuitry for the purposes and the scope of the system or apparatus claims.

The modules and units in the aforementioned description of the embodiments may be coupled to one another as described or as shown. The coupling may be direct or indirect, without or with intervening items between coupled modules or units. The coupling may be by physical contact or by communication between modules or units.

The above detailed description and embodiments of the disclosed system 100 are not intended to be exhaustive or to limit the disclosed system 100 to the precise form disclosed above. While specific examples for system 100 are described above for illustrative purposes, various equivalent modifications are possible within the scope of the disclosed system 100, as those skilled in the relevant art will recognize. For example, while processes and methods are presented in a given order, alternative implementations may perform routines having steps, or employ systems having processes or methods, in a different order, and some processes or methods may be deleted, moved, added, subdivided, combined, or modified to provide alternative or sub-combinations. Each of these processes or methods may be implemented in a variety of different ways. Also, while processes or methods are at times shown as being performed in series, these processes or blocks may instead be performed or implemented in parallel, or may be performed at different times.

The resulting method 300 and system 100 is cost-effective, highly versatile, and accurate, and may be implemented by adapting components for ready, efficient, and economical manufacturing, application, and utilization. Another important aspect of embodiments of the present disclosure is that it valuably supports and services the historical trend of reducing costs, simplifying systems, and/or increasing performance.

Identifiers, such as "(a)," "(b)," "(i)," "(ii)," etc., are sometimes used for different elements or steps. These identifiers are used for clarity and do not necessarily designate an order for the elements or steps.

These and other valuable aspects of the embodiments of the present disclosure consequently further the state of the technology to at least the next level. While the disclosed embodiments have been described as the best mode of implementing system 100, it is to be understood that many alternatives, modifications, and variations will be apparent to those skilled in the art in light of the descriptions herein. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A computer implemented method for integrating a workflow platform with an electronic health record system, the method comprising:
   (a) receiving, by one or more computing devices and from the electronic health record system, a context tag embedded in a screen of the electronic health record system that is currently being presented to a user, and wherein the context tag includes:
      an authentication parameter identifying the user accessing the screen, and
      a context identification parameter identifying a context of the screen;
   (b) authenticating, by the one or more computing devices, the user based on the authentication parameter;
   (c) based on authenticating the user, initiating, by the one or more computing devices, launch of the workflow platform, the workflow platform being a separate software application sidebar or panel on a client device that is used to consolidate patient health information found on different screens of the electronic health record system and present the patient health information of the electronic health record system;
   (d) populating, by the one or more computing devices, the workflow platform with customized interactive software applications integrated with the workflow platform based on the context identification parameter such that which customized software applications are retrieved depends on the context identification parameter; and
   wherein the context tag is a pixel embedded in the screen of the electronic health record system, wherein the pixel is implemented using SMART on FHIR technology.

2. The method of claim 1, wherein the customized interactive software applications are selected from the group consisting of applications for: telemedicine, videoconferencing, and analytic tools that access patent health information from the electronic health record system.

3. The method of claim 1, wherein authenticating in (b), initiating in (c), and populating in (d) are performed automatically upon receiving the context tag.

4. The method of claim 1, further comprising:
   receiving, by the one or more computing devices and via the electronic health record system, a user request requesting the initiating in (c); and
   wherein authenticating in (b), initiating in (c), and populating in (d) are performed based on receipt of the user request and the context tag.

5. The method of claim 1, further comprising:
   receiving, by the one or more computing devices and via the workflow platform, one or more inputs indicating updates to a health record of a patient; and
   updating, by the one or more computing devices, the electronic health record system based on the one or more inputs.

6. The method of claim 5, wherein updating the electronics health record system is performed in real-time from when the one or more inputs are received.

7. The method of claim 1, wherein the authentication parameter comprises an identifier obtained from a login screen of the electronic health record system that is encoded into the context tag of each screen of the electronic health record system.

8. A non-transitory computer readable medium including instructions for integrating a workflow platform with an electronic health record system, the instructions comprising:

(a) receiving, by one or more computing devices and from the electronic health record system, a context tag embedded in a screen of the electronic health record system that is currently being presented to a user, and wherein the context tag includes:
an authentication parameter identifying the user accessing the screen, and
a context identification parameter identifying a context of the screen;
(b) authenticating, by the one or more computing devices, the user based on the authentication parameter;
(c) based on authenticating the user, initiating, by the one or more computing devices, launch of the workflow platform, the workflow platform being a separate software application sidebar or panel on a client device that is used to consolidate patient health information found on different screens of the electronic health record system and present the patient health information of the electronic health record system;
(d) populating, by the one or more computing devices, the workflow platform with customized interactive software applications integrated with the workflow platform based on the context identification parameter such that which customized software applications are retrieved depends on the context identification parameter; and
wherein the context tag is a pixel embedded in the screen of the electronic health record system, wherein the pixel is implemented using SMART on FHIR technology.

9. The non-transitory computer readable medium of claim 8, with instructions wherein the customized interactive software applications are selected from the group consisting of applications for: telemedicine, videoconferencing, and analytic tools that access patent health information from the electronic health record system.

10. The non-transitory computer readable medium of claim 8, with instructions wherein authenticating in (b), initiating in (c), and populating in (d) are performed automatically upon receiving the context tag.

11. The non-transitory computer readable medium of claim 8, with instructions further comprising:
receiving, by the one or more computing devices and via the electronic health record system, a user request requesting the initiating in (c); and
wherein authenticating in (b), initiating in (c), and populating in (d) are performed based on receipt of the user request and the context tag.

12. The non-transitory computer readable medium of claim 8, with instructions further comprising:
receiving, by the one or more computing devices and via the workflow platform, one or more inputs indicating updates to a health record of a patient; and
updating, by the one or more computing devices, the electronic health record system based on the one or more inputs.

13. The non-transitory computer readable medium of claim 12, with instructions wherein updating the electronics health record system is performed in real-time from when the one or more inputs are received.

14. The non-transitory computer readable medium of claim 8, wherein the authentication parameter comprises an identifier obtained from a login screen of the electronic health record system that is encoded into the context tag of each screen of the electronic health record system.

15. A computing system for integrating a workflow platform with an electronic health record system comprising:
a communication unit including microelectronics to:
(a) receive, from the electronic health record system, a context tag embedded in a screen of the electronic health record system that is currently being presented to a user, and wherein the context tag includes:
an authentication parameter identifying the user accessing the screen, and
a context identification parameter identifying a context of the screen;
a memory, coupled to the communication unit, to store instructions;
a processor, coupled to the memory, to process the stored instructions to:
(b) authenticate the user based on the authentication parameter;
(c) based on authenticating the user, initiate launch of the workflow platform, the workflow platform being a separate software application sidebar or panel on a client device to consolidate patient health information found on different screens of the electronic health record system and present the patient health information of the electronic health record system;
(d) populate the workflow platform with customized interactive software applications integrated with the workflow platform based on the context identification parameter such that which customized software applications are retrieved depends on the context identification parameter; and
wherein the context tag is a pixel embedded in the screen of the electronic health record system, wherein the pixel is implemented using SMART on FHIR technology.

16. The computing system of claim 15, wherein the processor is further configured to authenticate in (b), initiate in (c), and populate in (d) automatically upon receiving the context tag.

17. The computing system of claim 15, wherein:
the communication unit is further configured to receive, via the electronic health record system, a user request requesting the initiating in (c); and
the processor is further configured to authenticate in (b), initiate in (c), and populate in (d) based on receipt of the user request and the context tag.

18. The computing system of claim 15, wherein:
the communication unit is further configured to receive, via the workflow platform one or more inputs indicating updates to a health record of a patient; and
the processor is further configured to update the electronic health record system based on the one or more inputs.

19. The computing system of claim 18, wherein the processor is further configured to update the electronics health record system in real-time from when the one or more inputs are received.

20. The computing system of claim 15, wherein the authentication parameter comprises an identifier obtained from a login screen of the electronic health record system that is encoded into the context tag of each screen of the electronic health record system.

* * * * *